US00PP22767P2

(12) United States Plant Patent
Kolster

(10) Patent No.: US PP22,767 P2
(45) Date of Patent: Jun. 5, 2012

(54) *POTENTILLA* PLANT NAMED 'RED LADY'

(50) Latin Name: *Potentilla fruticosa*
Varietal Denomination: Red Lady

(75) Inventor: Pieter Kolster, Boskoop (NL)

(73) Assignee: Spring Meadow Nursery, Inc., Grand Haven, MI (US)

( * ) Notice: Subject to any disclaimer, the term of this patent is extended or adjusted under 35 U.S.C. 154(b) by 189 days.

(21) Appl. No.: 12/799,432

(22) Filed: Apr. 23, 2010

(51) Int. Cl.
*A01H 5/00* (2006.01)

(52) U.S. Cl. ..... Plt./237

(58) Field of Classification Search ..... Plt./237
See application file for complete search history.

(56) References Cited

OTHER PUBLICATIONS

UPOV ROM GTITM Computer Database, GTI JOUVE Retrieval Software 2011/10 Citation for 'Red Lady'.*

* cited by examiner

*Primary Examiner* — Wendy C Haas
(74) *Attorney, Agent, or Firm* — C. A. Whealy

(57) ABSTRACT

A new and distinct cultivar of *Potentilla* plant named 'Red Lady', characterized by its upright and somewhat outwardly spreading plant habit; freely branching habit; large red-colored flowers that maintain red coloration during the summer; and good garden performance.

2 Drawing Sheets

Botanical designation: *Potentilla fruticosa.*
Cultivar denomination: 'RED LADY'.

BACKGROUND OF THE INVENTION

The present invention relates to a new and distinct cultivar of *Potentilla* plant, botanically known as *Potentilla fruticosa*, and hereinafter referred to by the name 'Red Lady'.

The new *Potentilla* plant is a product of a planned breeding program conducted by the Inventor in Boskoop, The Netherlands. The objective of the breeding program was to develop new *Potentilla* plants with red-colored flowers that maintain red coloration during the summer.

The new *Potentilla* plant originated from a self-pollination in July, 2004 of *Potentilla fruticosa* 'Marion Red Robbin', not patented. The new *Potentilla* plant was discovered and selected by the Inventor in August, 2005 as a flowering plant within the progeny of the stated self-pollination in a controlled environment in Boskoop, The Netherlands.

Asexual reproduction of the new *Potentilla* plant by vegetative cuttings in a controlled environment in Boijl, The Netherlands since June, 2006, has shown that the unique features of this new *Potentilla* plant are stable and reproduced true to type in successive generations.

SUMMARY OF THE INVENTION

Plants of the new *Potentilla* have been observed under all possible cultural and environmental conditions. The phenotype may vary somewhat with variations in cultural practices and environment such as temperature and light intensity without, however, any variance in genotype.

The following traits have been repeatedly observed and are determined to be the unique characteristics of 'Red Lady'. These characteristics in combination distinguish 'Red Lady' as a new and distinct *Potentilla* plant:

1. Upright and somewhat outwardly spreading plant habit.
2. Freely branching habit.

3. Large red-colored flowers that maintain red coloration during the summer.
4. Good garden performance.

Plants of the new *Potentilla* can be compared to plants of the parent, 'Marion Red Robbin'. Plants of the new *Potentilla* differ primarily from plants of 'Marion Red Robbin' in the following characteristics:

1. Plants of the new *Potentilla* are more spreading than plants of 'Marion Red Robbin'.
2. Plants of the new *Potentilla* are more freely flowering than plants of 'Marion Red Robbin'.
3. During the summer, flowers of plants of the new *Potentilla* maintain red coloration whereas flowers of plants of 'Marion Red Robbin' become orange red in color.

Plants of the new *Potentilla* can be compared to plants of *Potentilla fruticosa* 'White Lady', disclosed in U.S. Plant patent application No. 12/799,431. Plants of the new *Potentilla* differ primarily from plants of 'White Lady' in flower color as plants of 'White Lady' have white-colored flowers.

BRIEF DESCRIPTION OF THE PHOTOGRAPHS

The accompanying colored photographs illustrate the overall appearance of the new *Potentilla* plant, showing the colors as true as it is reasonably possible to obtain in colored reproductions of this type. Colors in the photographs may differ slightly from the color values cited in the detailed botanical description which accurately describe the colors of the new *Potentilla* plant.

The photograph on the first sheet comprises a side perspective view of a typical flowering plant of 'Red Lady' grown in a container.

The photograph at the top of the second sheet is a close-up view of typical leaves and stems of 'Red Lady'.

The photograph at the bottom of the second sheet is a close-up view of a typical flowering stem of 'Red Lady'.

DETAILED BOTANICAL DESCRIPTION

The aforementioned photographs and following observations, measurements and values describe plants grown in two-liter containers during the autumn in an outdoor nursery in Boskoop, The Netherlands and under conditions which closely approximate commercial *Potentilla* production. During the production of the plants, day temperatures ranged from 8° C. to 18° C. and night temperatures ranged from 1° C. to 12° C. Plants were two years old when the photographs and the description were taken. In the description, color references are made to The Royal Horticultural Society Colour Chart, 2007 Edition, except where general terms of ordinary dictionary significance are used.

*Botanical classification: Potentilla fruticosa* 'Red Lady'.

Parentage: Self-pollination of *Potentilla fruticosa* 'Marion Red Robbin', not patented.

Propagation:

*Type*.—By vegetative cuttings.

*Time to initiate roots*.—About 21 to 25 days at 20° C.

*Time to develop roots*.—About three months at 20° C.

*Root description*.—Fine, fibrous; brown in color.

*Rooting habit*.—Freely branching.

Plant description:

*Plant form and growth habit*.—Perennial deciduous shrub; upright and somewhat outwardly spreading plant habit, roughly globular in shape; moderately vigorous growth habit.

*Branching habit*.—Freely branching habit, usually about 52 lateral branches develop per plant; pinching enhances lateral branch development.

*Plant height*.—About 25.1 cm.

*Plant diameter* (*area of spread*).—About 33.6 cm.

Lateral branch description:

*Length*.—About 11 cm.

*Diameter*.—About 1 mm.

*Internode length*.—About 6 mm.

*Strength*.—Strong.

*Texture*.—Pubescent, rough; woody with development.

*Color, developing*.—Close to 165A.

*Color, woody*.—Close to 200B.

Foliage description:

*Arrangement*.—Alternate; palmately compound with three leaflets per leaf; leaflets sessile.

*Leaf length*.—About 1.4 cm.

*Leaf width*.—About 2.1 cm.

*Leaflet length*.—About 1.1 cm.

*Leaflet width*.—About 4 mm.

*Leaflet shape*.—Narrowly obovate.

*Leaflet apex*.—Apiculate.

*Leaflet base*.—Attenuate.

*Leaflet margin*.—Entire.

*Leaflet texture, upper and lower surfaces*.—Pubescent.

*Leaflet venation pattern*.—Pinnate.

*Leaflet color*.—Developing leaflets, upper surface: Close to 137B. Developing leaflets, lower surface: Close to 138B. Mature leaflets, upper surface: Close to N137B; venation, close to N137B. Mature leaflets, lower surface: Close to 138B; venation, close to 191B.

*Leaf petiole*.—Length: About 4 mm. Diameter: About 0.75 mm. Texture, upper and lower surfaces: Smooth, glabrous. Color, upper and lower surfaces: Close to 143C.

Flower description:

*Flower arrangement, shape and habit*.—Single rotate flowers, flowers usually terminal and sometimes in pairs; flowers face upright; freely flowering habit, about six flowers and flower buds per lateral branch.

*Fragrance*.—None detected.

*Natural flowering season*.—Plants begin flowering about 7.5 months after planting and flower from the late spring into the autumn in The Netherlands.

*Flower longevity on the plant*.—About five days; flowers not persistent.

*Flower buds*.—Length: About 4 mm. Diameter: About 4 mm. Shape: Flattened globular. Color: Close to 145B to 145C.

*Flowers*.—Diameter: About 2.8 cm. Depth (height): About 9 mm.

Petals.—Arrangement: Five in a single whorl. Length: About 1.4 cm. Width: About 1.4 cm. Shape: Orbicular; slightly concave. Apex: Obtuse to retuse. Base: Attenuate. Margin: Entire. Texture, upper and lower surfaces: Smooth, glabrous. Color: When opening, upper surface: Close to 45B. When opening, lower surface: Close to 10C to 10D. Fully opened, upper surface: Between 42A and 45B; color does not fade with development or under high temperatures during the summer. Fully opened, lower surface: Close to 10C to 10D.

*Petaloids*.—Occurrence: About 60% of the flowers have a single petaloid. Length: About 1.1 cm. Width: About 7 mm. Shape: Obovate. Margin: Entire. Texture, upper and lower surfaces: Smooth, glabrous. Color: When opening, upper surface: Close to 45B. When opening, lower surface: Close to 10C to 10D. Fully opened, upper surface: Between 42A and 45B; color does not fade with development or under high temperatures during the summer. Fully opened, lower surface: Close to 10C to 10D.

*Sepals*.—Arrangement: Five in a single whorl. Length: About 5 mm. Width: About 3 mm. Shape: Ovate. Apex: Acute. Base: Broadly cuneate. Margin: Entire. Texture, upper and lower surfaces: Smooth, glabrous. Color: Immature, upper and lower surfaces: Close to 145B to 145C. Mature, upper and lower surfaces: Close to 145B to 145C; towards the margins, close to 165B.

*Pedicels*.—Strength: Moderately strong. Length: About 4 mm. Diameter: About 0.75 mm. Aspect: Erect. Texture: Smooth, glabrous. Color: Close to 147D.

*Reproductive organs*.—Stamens: Quantity per flower: About 25. Filament length: About 2 mm. Anther size: About 1 mm by 0.5 mm. Anther shape: Ovate. Anther color: Close to 14A to 14B. Pollen amount: Scarce. Pollen color: Close to 22A. Pistils: Quantity per flower: About 30. Pistil length: About 1.5 mm. Stigma color: Greyed red. Style length: About 1.2 mm. Style color: Close to 144B to 144C. Ovary color: Close to 144B to 144C.

Temperature tolerance: Plants of the new *Potentilla* have been observed to be hardy to USDA Hardiness Zone 3 and to tolerate high temperatures of about 40° C.

Pathogen/pest resistance: Plants of the new *Potentilla* have not been shown to be resistant to pathogens and pests common to *Potentilla*.

It is claimed:

1. A new and distinct *Potentilla* plant named 'Red Lady' as illustrated and described.

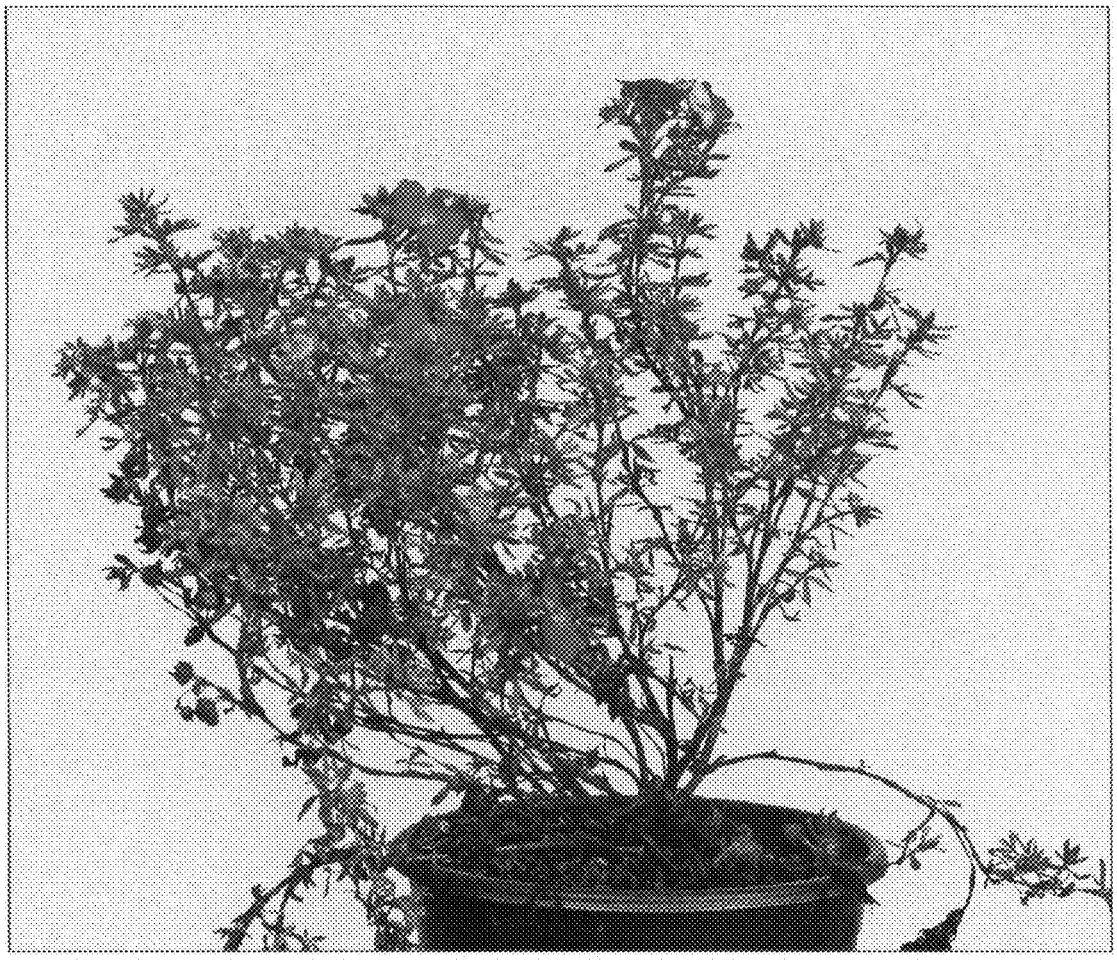

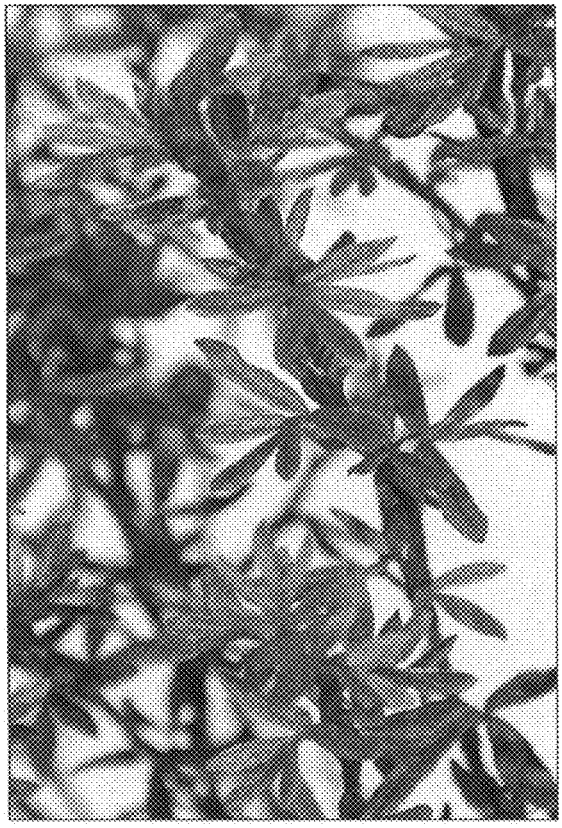
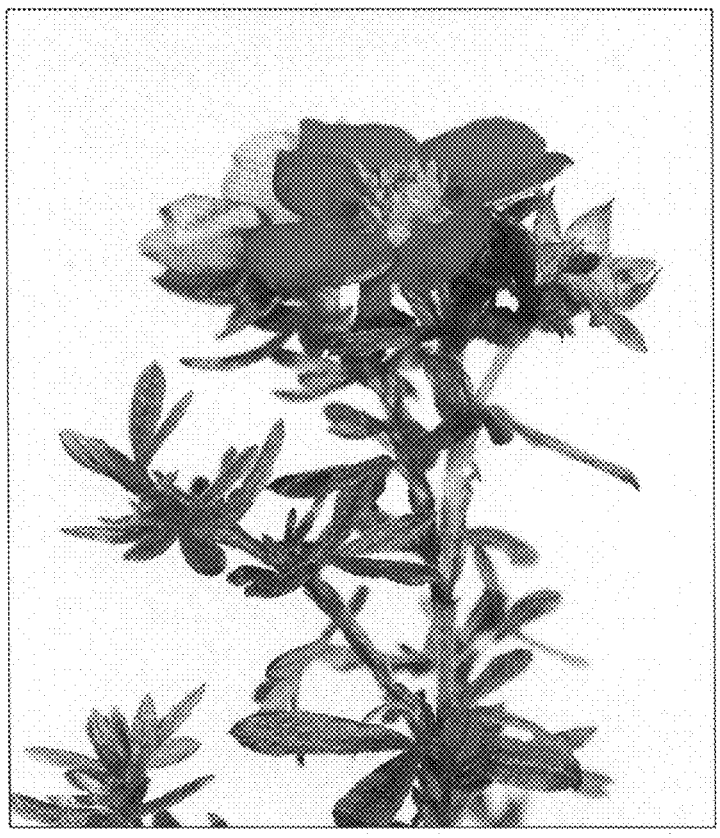

* * * * *